(12) United States Patent
Applegate et al.

(10) Patent No.: US 11,786,229 B2
(45) Date of Patent: *Oct. 17, 2023

(54) INTELLIGENT ADAPTER ASSEMBLY FOR USE WITH AN ELECTROMECHANICAL SURGICAL SYSTEM

(71) Applicant: Covidien LP, Mansfield, MA (US)

(72) Inventors: Robert Applegate, Wallingford, CT (US); David M. McCuen, Stratford, CT (US)

(73) Assignee: Covidien LP, Mansfield, MA (US)

( * ) Notice: Subject to any disclaimer, the term of this patent is extended or adjusted under 35 U.S.C. 154(b) by 192 days.

This patent is subject to a terminal disclaimer.

(21) Appl. No.: 17/176,526

(22) Filed: Feb. 16, 2021

(65) Prior Publication Data

US 2021/0161514 A1    Jun. 3, 2021

Related U.S. Application Data

(63) Continuation of application No. 14/134,316, filed on Dec. 19, 2013, now Pat. No. 10,918,364.

(Continued)

(51) Int. Cl.
*A61B 17/00* (2006.01)
*A61B 17/115* (2006.01)
(Continued)

(52) U.S. Cl.
CPC ............ *A61B 17/00* (2013.01); *A61B 17/072* (2013.01); *A61B 17/115* (2013.01);
(Continued)

(58) Field of Classification Search
CPC .. A61B 2017/00734; A61B 2017/0046; A61B 2017/293; A61B 17/00; A61B 17/072; A61B 17/115; A61B 17/2804
See application file for complete search history.

(56) References Cited

U.S. PATENT DOCUMENTS 2,957,353 A    10/1960  Babacz
3,111,328 A    11/1963  Di Rito et al.
(Continued)

FOREIGN PATENT DOCUMENTS

AU    2008229795 A1    4/2009
CA       2451558 A1    1/2003
(Continued)

OTHER PUBLICATIONS

International Search Report corresponding to PCT/US2005/027266, completed May 30, 2008 and dated Jun. 18, 2008; (2 pp.).

(Continued)

*Primary Examiner* — Lynsey C Eiseman
*Assistant Examiner* — Amanda L. Steinberg
(74) *Attorney, Agent, or Firm* — Carter, DeLuca & Farrell LLP

(57) ABSTRACT

An adapter assembly is provided and includes a housing for connection with a surgical device and for operative communication with at least one rotatable drive shaft of the surgical device; an outer tube having a proximal end supported by the housing and a distal end for connection with a selected end effector, wherein the distal end of the outer tube is in operative communication with each of the at least one force receiving drive member of the end effector; at least one drive transmitting/converting assembly for interconnecting a respective one of the at least one rotatable drive shaft of the surgical device and one of the at least one force receiving drive member of the end effector; and a circuit board supported in the housing and storing at least one of operating parameters and life cycle information which are unique to the adapter assembly.

17 Claims, 14 Drawing Sheets

Related U.S. Application Data

(60) Provisional application No. 61/756,101, filed on Jan. 24, 2013.

(51) Int. Cl.
*A61B 17/072* (2006.01)
*A61B 90/00* (2016.01)

(52) U.S. Cl.
CPC ............. *A61B 2017/0046* (2013.01); *A61B 2017/00734* (2013.01); *A61B 2090/0803* (2016.02); *A61B 2090/0804* (2016.02); *A61B 2090/0807* (2016.02); *A61B 2560/0443* (2013.01)

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Mesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |

(56) References Cited

U.S. PATENT DOCUMENTS

| | | |
|---|---|---|
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,278 B2 | 3/2015 | Tovey et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0267297 A1* | 12/2004 | Malackowski ........ A61B 90/98 606/1 |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |

(56) References Cited

U.S. PATENT DOCUMENTS

| | | |
|---|---|---|
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1* | 5/2012 | Bryant ............. A61B 17/07207 227/175.1 |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101090677 A | 12/2007 |
| CN | 101856251 A | 10/2010 |
| CN | 102113902 A | 7/2011 |
| CN | 102247182 A | 11/2011 |
| CN | 103961148 B | 2/2019 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 B1 | 6/2012 |
| EP | 2491872 A1 | 8/2012 |

(56) References Cited

FOREIGN PATENT DOCUMENTS

| | | |
|---|---|---|
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2684529 A2 | 1/2014 |
| EP | 2815705 A1 | 12/2014 |
| ES | 2333509 A1 | 2/2010 |
| FR | 2861574 A1 | 5/2005 |
| JP | 324220 | 1/1996 |
| JP | 08038488 | 2/1996 |
| JP | 2005125075 A | 5/2005 |
| JP | 2009028157 A | 2/2009 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007/026354 A1 | 3/2007 |
| WO | 2007137304 A2 | 11/2007 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012/040984 A1 | 4/2012 |

OTHER PUBLICATIONS

Extended European Search Report corresponding to EP 08 25 2703.7, completed Oct. 23, 2008 and dated Oct. 31, 2008; (7 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
Extended European Search Report corresponding to Application No. EP 14152236.7 dated May 12, 2014.
EP Office Action for EP 14152236.7 dated Aug. 11, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.

(56) References Cited

OTHER PUBLICATIONS

European Office Action corresponding to International Application No. EP 14 15 2236.7 dated Aug. 11, 2015.
Extended European Search Report corresponding to International Application No. EP 15 18 4915.5 dated Jan. 5, 2016.
European Communication issued in European Patent Application No. 14152236.7 dated Sep. 29, 2016, 4 pages.
Chinese Office Action dated Dec. 27, 2016 in corresponding Chinese Patent Application No. 201410036559.X together with English translation, 29 pages.
Australian Examination Report for application No. 2014200176 dated Jun. 30, 2017.
European Office Action dated Oct. 27, 2017 issued in corresponding EP Appln. No. 14152236.7.
Japanese Office Action dated Oct. 24, 2017 issued in corresponding Japanese Appln. No. 2014-011079.
Chinese Office Action dated Apr. 13, 2018 issued in corresponding Chinese Appln. No. 201410036559X.
Japanese Office Action dated Jun. 26, 2018 issued in corresponding JP Appln. No. 2014-011079.
Canadian Office Action dated Oct. 4, 2019 issued in corresponding CA Appln. No. 2,839,910.
Chinese Office Action dated Oct. 28, 2020 issued in corresponding CN Appln. No. 2018115817367.

* cited by examiner

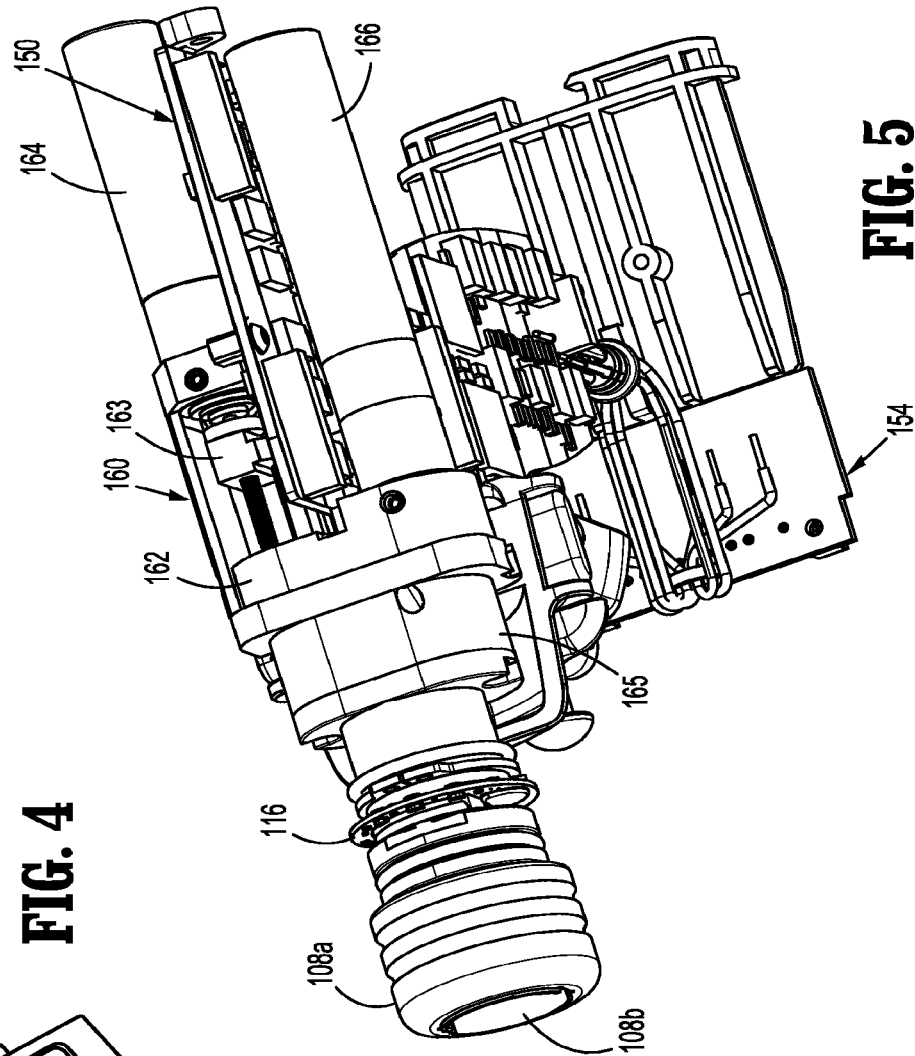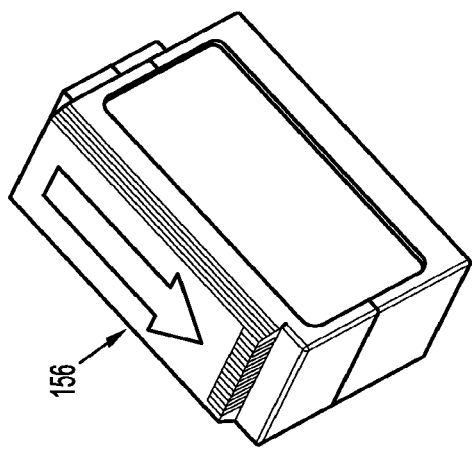

INTELLIGENT ADAPTER ASSEMBLY FOR USE WITH AN ELECTROMECHANICAL SURGICAL SYSTEM

CROSS-REFERENCE TO RELATED APPLICATIONS

This application is a continuation of U.S. patent application Ser. No. 14/134,316, filed Dec. 19, 2013, which claims the benefit of and priority to U.S. Provisional Patent Application No. 61/756,101, filed Jan. 24, 2013. The entire disclosures of the foregoing applications are incorporated by reference herein.

BACKGROUND

1. Technical Field

The present disclosure relates to adapter assemblies for use with an electromechanical surgical system and their methods of use. More specifically, the present disclosure relates to intelligent adapter assemblies for use between hand-held, electromechanical surgical devices and end effectors.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary drive systems for operating and/or manipulating the surgical device. In many instances the surgical devices include a handle assembly, which is reusable, and a disposable end effector or the like that is selectively connected to the handle assembly prior to use and then disconnected from the end effector following use in order to be disposed of or in some instances sterilized for re-use.

Many of the existing end effectors for use with many of the existing surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with surgical devices and/or handle assemblies that use a rotary motion to deliver power, a need exists for adapters and/or adapter assemblies to interface between and interconnect the linear driven end effectors with the rotary driven electromechanical surgical devices and/or handle assemblies.

Additionally, a need exists for various type of adapter assemblies to store and/or retain relevant information pertaining to the safe and effective operation of the adapter assembly.

SUMMARY

The present disclosure relates to intelligent adapter assemblies for use between hand-held, electromechanical surgical devices and end effectors.

According to an aspect of the present disclosure, an adapter assembly is provided for selectively interconnecting a surgical end effector that is configured to perform a surgical function and an electromechanical surgical device that is configured to actuate the end effector, the end effector including at least one force receiving drive member, and the surgical device including at least one rotatable drive shaft.

The adapter assembly comprises a housing configured and adapted for connection with the surgical device and to be in operative communication with each of the at least one rotatable drive shaft of the surgical device; an outer tube having a proximal end supported by the housing and a distal end configured and adapted for connection with the end effector, wherein the distal end of the outer tube is in operative communication with each of the at least one force receiving drive member of the end effector; at least one drive transmitting/converting assembly for interconnecting a respective one of the at least one rotatable drive shaft of the surgical device and one of the at least one force receiving drive member of the end effector; and a circuit board supported in the housing and storing at least one of operating parameters and life cycle information which are unique to the adapter assembly.

The operating parameters for the adapter assembly may include at least identification information relating to the adapter assembly; dimensions of the adapter assembly; specific designations for which rotational input received from the surgical device will perform which specific function in the adapter assembly; and a maximum force that can be delivered from the surgical device to the adapter assembly.

The identification information may include at least a model number and a serial number.

The life-cycle information for the adapter assembly may include at least one of a number of revolutions experienced by an input force receiving member of the adapter assembly; a number of cleaning cycles of the adapter assembly; an assembly date of the adapter assembly; and any repair/maintenance dates of the shaft assembly.

The adapter assembly may further include at least one electrical contact supported in the housing and being configured to interface with the surgical device.

The at least one drive transmitting/converting assembly may include a first end that is releasably connectable to a first rotatable drive shaft of the surgical device and a second end that is releasably connectable to the at least one force receiving drive member of the end effector. The at least one drive transmitting/converting assembly may convert and transmit a rotation of the first rotatable drive shaft of the surgical device to an axial translation of the at least one force receiving drive member of the end effector.

According to another aspect of the present disclosure, an electromechanical surgical system for performing at least one surgical procedure is provided. The electromechanical surgical system includes an electromechanical surgical device and a plurality of surgical end effectors. The electromechanical surgical system further comprises at least a pair of unique, diverse adapter assemblies, wherein each adapter assembly includes a housing configured and adapted for connection with the surgical device and to be in operative communication with each of the at least one rotatable drive shaft of the surgical device; an outer tube having a proximal end supported by the housing and a distal end configured and adapted for connection with the end effector, wherein the distal end of the outer tube is in operative communication with each of the at least one force receiving drive member of the end effector; at least one drive transmitting/converting assembly for interconnecting a respective one of the at least one rotatable drive shaft of the surgical device and one of the at least one force receiving drive member of the end effector; and a circuit board supported in the housing and storing at least one of operating parameters and life cycle information which are unique to the adapter assembly.

The operating parameters for each adapter assembly may include at least identification information relating to the adapter assembly; dimensions of the adapter assembly; specific designations for which rotational input received from the surgical device will perform which specific function in the adapter assembly; and a maximum force that can be delivered from the surgical device to the adapter assembly.

The identification information may include at least a model number and a serial number.

The electromechanical surgical system according to claim 8, wherein the life-cycle information for each adapter assembly may include at least one of a number of revolutions experienced by an input force receiving member of the adapter assembly; a number of cleaning cycles of the adapter assembly; an assembly date of the adapter assembly; and any repair/maintenance dates of the shaft assembly.

Each adapter assembly may include at least one electrical contact supported in the housing and being configured to interface with the surgical device.

The at least one drive transmitting/converting assembly of each adapter assembly may include a first end that is releasably connectable to a first rotatable drive shaft of the surgical device and a second end that is releasably connectable to the at least one force receiving drive member of the end effector. The at least one drive transmitting/converting assembly may convert and transmit a rotation of the first rotatable drive shaft of the surgical device to an axial translation of the at least one force receiving drive member of the end effector.

According to yet another aspect of the present disclosure, a method of performing a surgical procedure is provided and comprises the steps of providing an electromechanical surgical system, the electromechanical surgical system including a plurality of surgical end effectors, each being configured to perform a surgical function, each end effector including at least one force receiving drive member; an electromechanical surgical device configured to actuate each of the plurality of end effectors, the electromechanical surgical device including at least one rotatable drive shaft; and a plurality of unique, diverse adapter assemblies for selectively interconnecting a selected one of the plurality of surgical end effectors and the electromechanical surgical device.

Each adapter assembly includes a housing configured and adapted for connection with the surgical device and to be in operative communication with each of the at least one rotatable drive shaft of the surgical device; an outer tube having a proximal end supported by the housing and a distal end configured and adapted for connection with the end effector, wherein the distal end of the outer tube is in operative communication with each of the at least one force receiving drive member of the end effector; at least one drive transmitting/converting assembly for interconnecting a respective one of the at least one rotatable drive shaft of the surgical device and one of the at least one force receiving drive member of the end effector; and a circuit board supported in the housing and storing at least one of operating parameters and life cycle information which are unique to the adapter assembly.

The method includes the steps of selecting a surgical end effector for performing a surgical procedure; selecting a proper adapter assembly for interconnecting the selected end effector and the surgical device; connecting the selected adapter assembly to the surgical device; and communicating at least one of operating parameters and life cycle information, of the selected adapter assembly, to the surgical device.

The method may further include the step of processing the communicated at least one of operating parameters and life cycle information, of the selected adapter assembly.

The method may further include the step of setting operating parameters for the surgical device based on the at least one of operating parameters and life cycle information communicated from the selected adapter assembly.

The method may further include the step of creating a signal in response to the processing the communicated at least one of operating parameters and life cycle information of the selected adapter assembly, providing an indication of a readiness of at least one of the selected adapter assembly and the surgical device.

The method may further include the step of connecting the selected end effector to the selected adapter assembly.

The method may further include the step of updating at least one of operating parameters and life cycle information of the selected adapter assembly at least one of before, during and after the surgical procedure.

BRIEF DESCRIPTION OF THE DRAWINGS

Embodiments of the present disclosure are described herein with reference to the accompanying drawings, wherein:

FIG. 4 is a perspective view of a battery for use in the surgical device of FIGS. 1-3;

FIG. 5 is a perspective view of the surgical device of FIGS. 1-3, with a housing thereof removed;

DETAILED DESCRIPTION OF EMBODIMENTS

Figure 1:
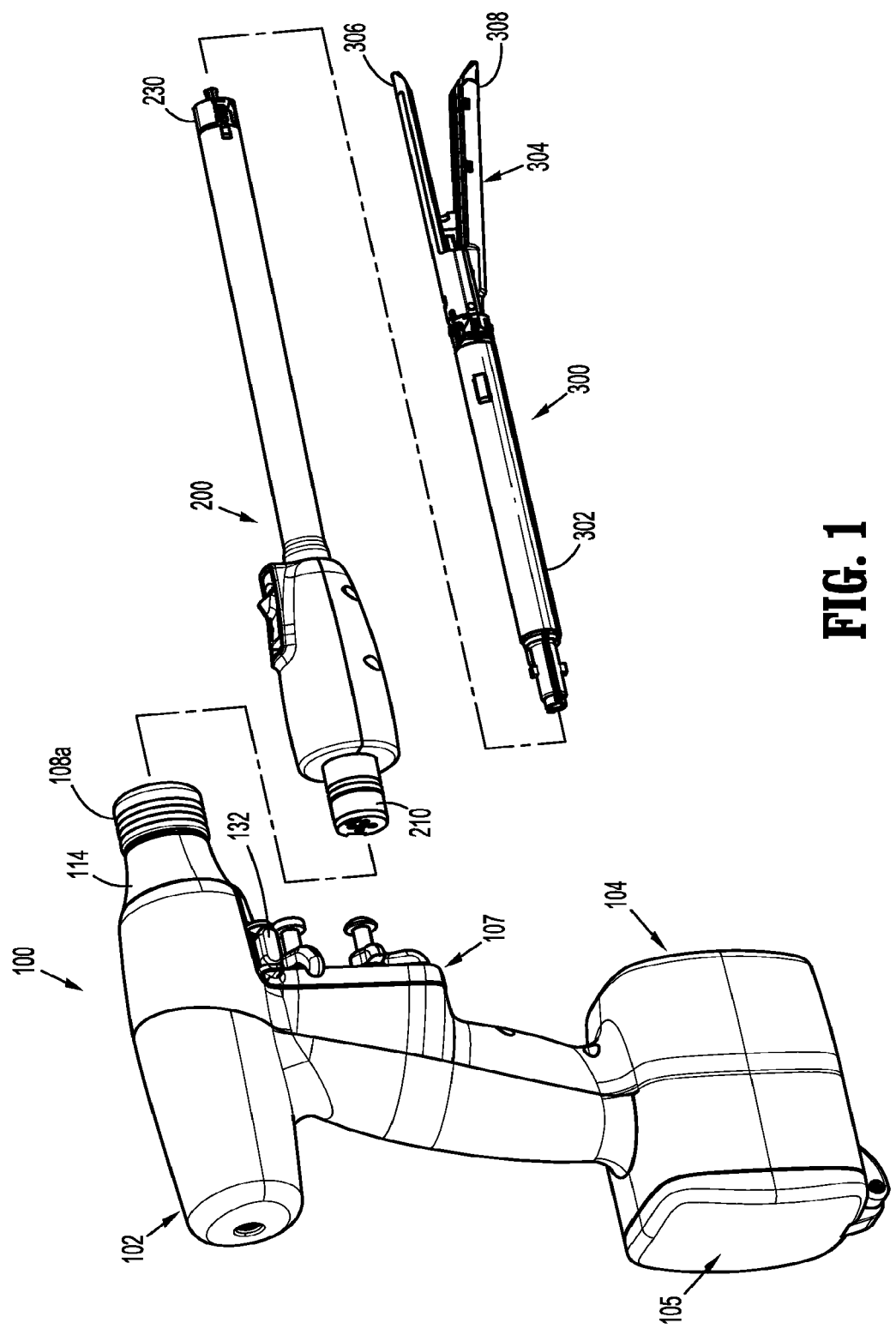
FIG. 1 is a perspective view, with parts separated, of a hand-held, electromechanical surgical device and adapter assembly, in accordance with an embodiment of the present disclosure, illustrating a connection thereof with an end effector.

Embodiments of the presently disclosed surgical devices, and adapter assemblies for electromechanical surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered, hand-held, electromechanical instrument configured for selective attachment thereto of a plurality of different end effectors that are each configured for actuation and manipulation by the powered, hand-held, electromechanical surgical instrument.

As illustrated in FIG. 1, surgical device 100 is configured for selective connection with any one of a number of adapter assemblies 200 (whether intelligent or not intelligent, i.e., dumb), and, in turn, each unique adapter assembly 200 is configured for selective connection with any number of unique end effectors or single use loading units 300.

Figure 2:
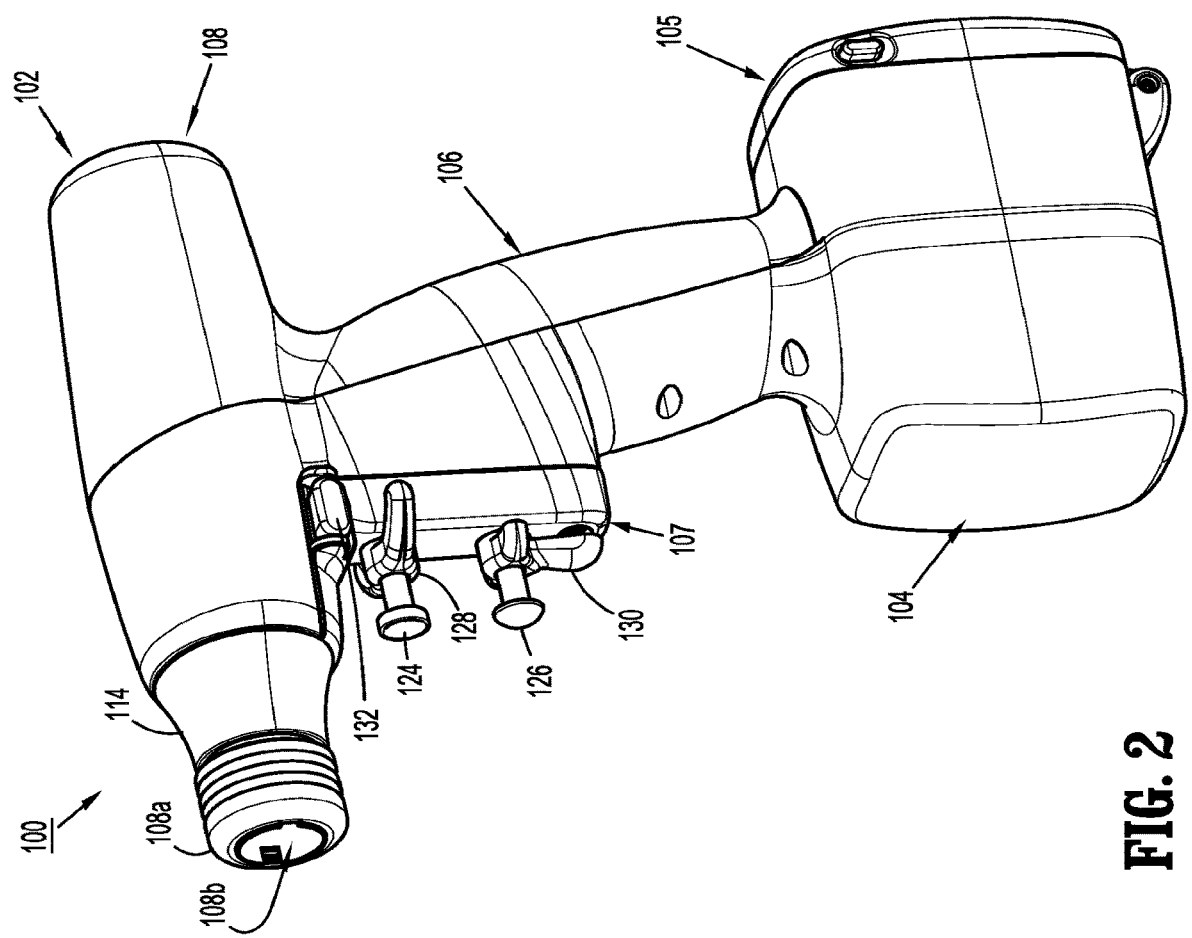
FIG. 2 is a perspective view of the surgical device of FIG. 1.
Figure 3:
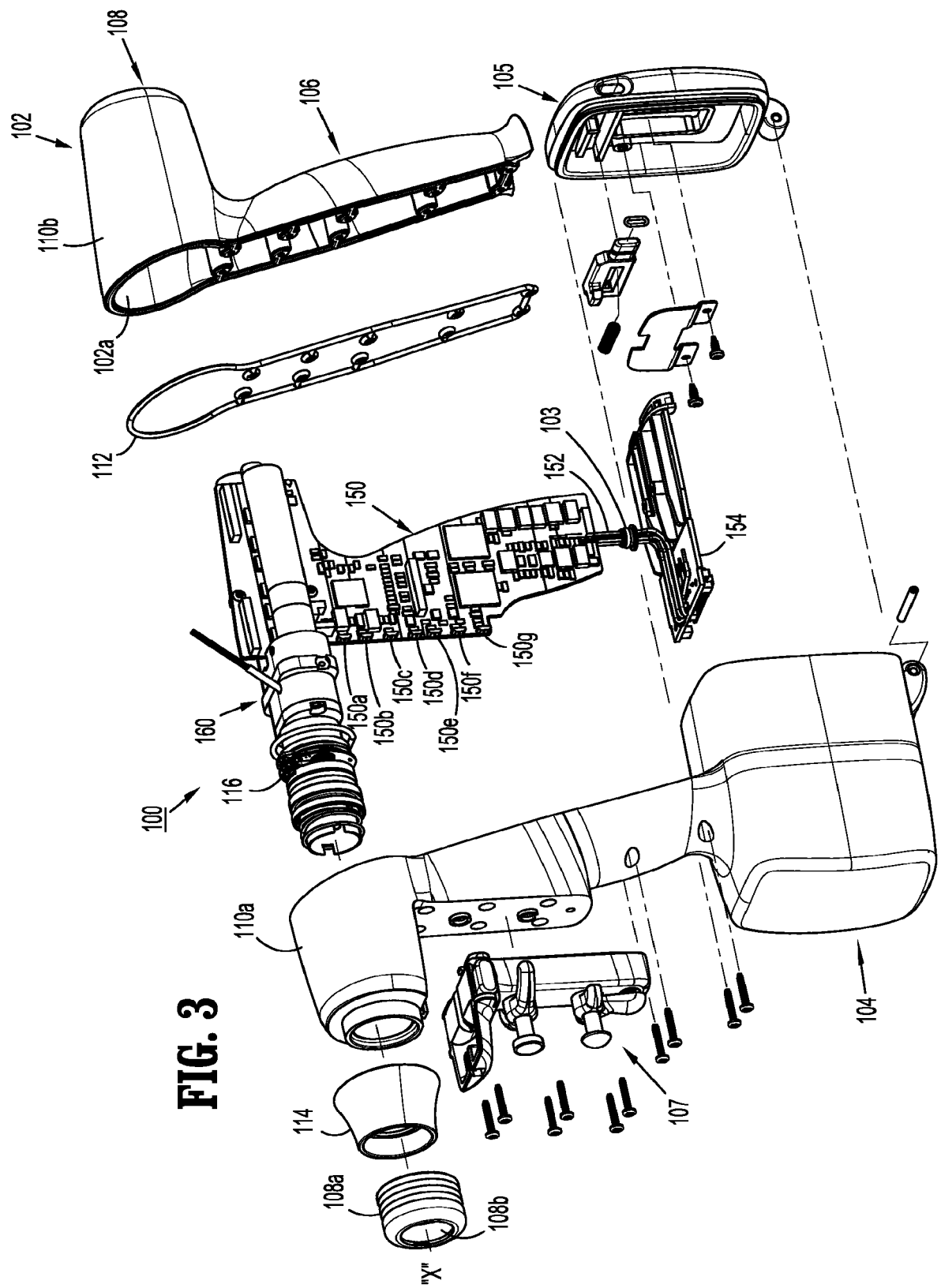
FIG. 3 is a perspective view, with parts separated, of the surgical device of FIGS. 1 and 2.

As illustrated in FIGS. 1-3, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIG. 1.

Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical device 100, as will be set forth in additional detail below.

Lower housing portion 104 of surgical device 100 defines an aperture (not shown) formed in an upper surface thereof and which is located beneath or within intermediate housing portion 106. The aperture of lower housing portion 104 provides a passage through which wires 152 pass to electrically interconnect electrical components (a battery 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 (not shown) thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable battery 156, is removably situated. Battery 156 is configured to supply power to any of the electrical components of surgical device 100. Lower housing portion 104 defines a cavity (not shown) into which battery 156 is inserted. Lower housing portion 104 includes a door 105 pivotally connected thereto for closing cavity of lower housing portion 104 and retaining battery 156 therein. While a battery 156 is shown, it is contemplated that the surgical device may be powered by any number of power sources, such as, for example, a fuel cell, a power cord connected to an external power source, etc.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 is in the form of a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical device 100. In particular, drive mechanism 160 is configured to drive shafts and/or gear components in order to selectively move tool assembly 304 of end effector 300 (see FIGS. 1 and 20) relative to proximal body portion 302 of end effector 300, to rotate end effector 300 about a longitudinal axis "X" (see FIG. 3) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter assembly 200. Proximal to the selector gearbox assembly 162 is a function selection module 163 having a first motor 164 that functions to selectively move gear elements within the selector gearbox assembly 162 into engagement with an input drive component 165 having a second motor 166.

As illustrated in FIGS. 1-4, and as mentioned above, distal half-section 110a of upper housing portion 108 defines a connecting portion 108a configured to accept a corresponding drive coupling assembly 210 of adapter assembly 200.

Figure 6:
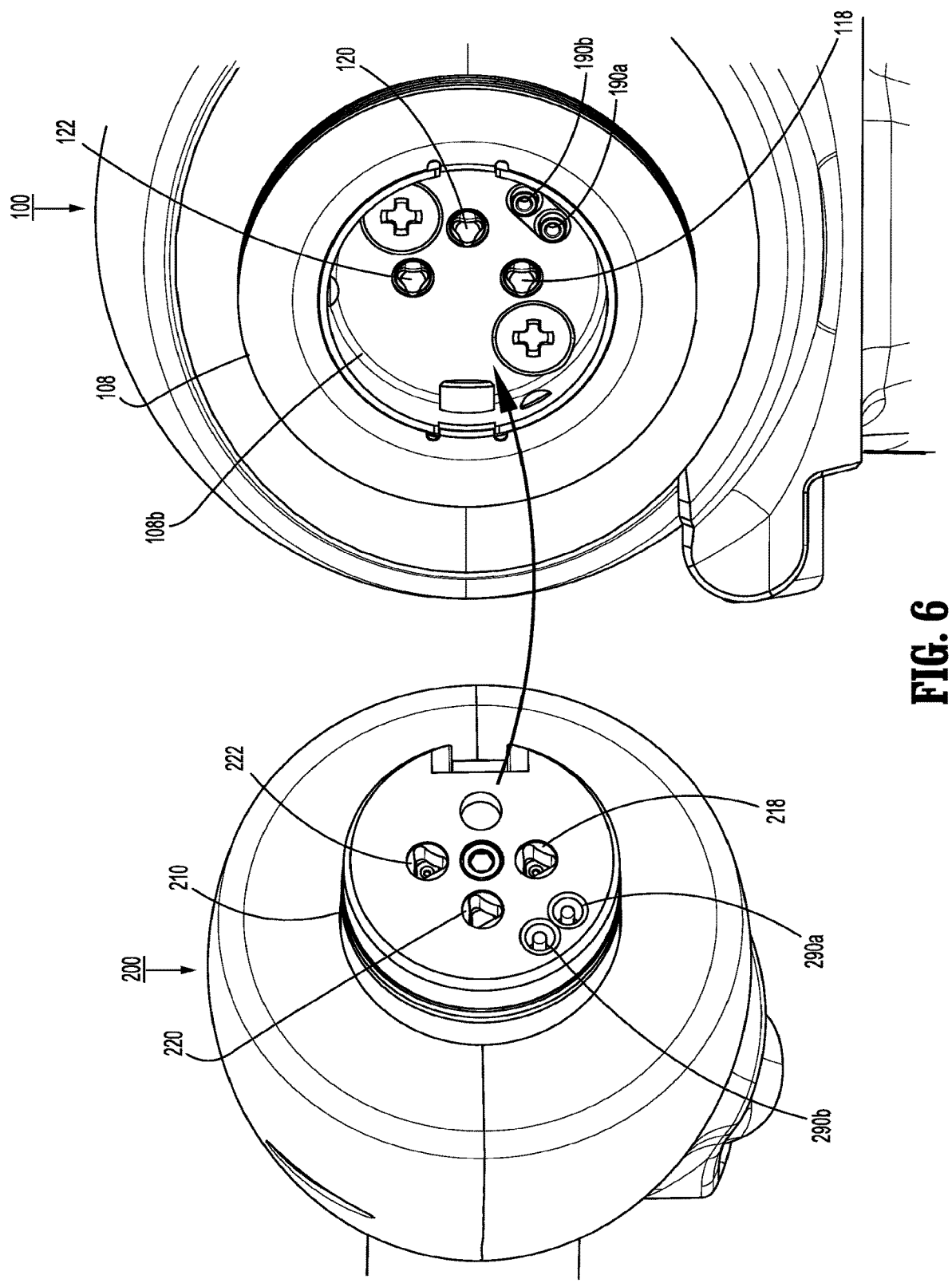
FIG. 6 is a perspective view of the connecting ends of each of the surgical device and the adapter assembly, illustrating a connection therebetween.
Figure 7:
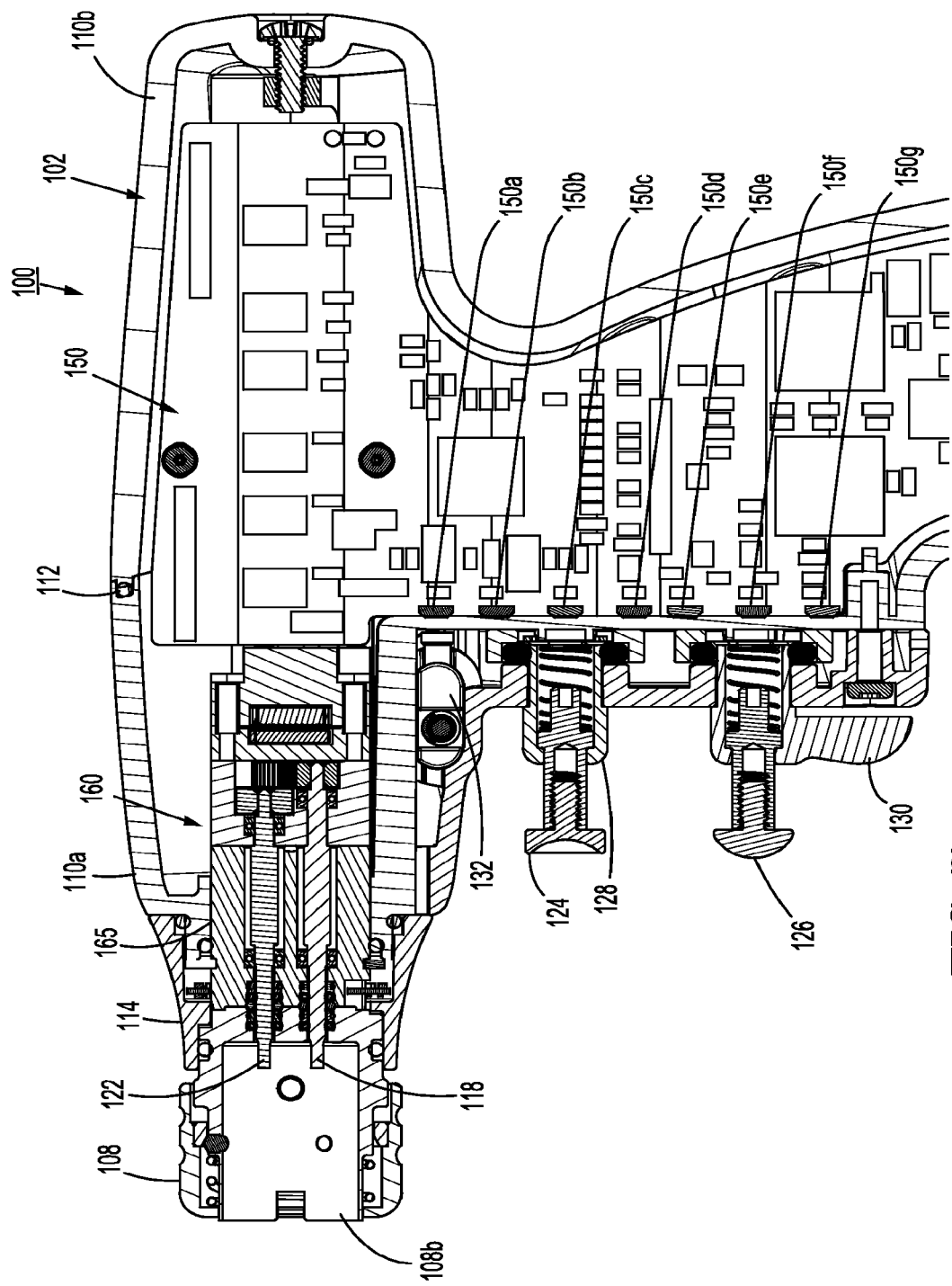
FIG. 7 is a cross-sectional view of the surgical device of FIGS. 1-3, as taken through 7-7 of FIG. 2.
Figure 8:
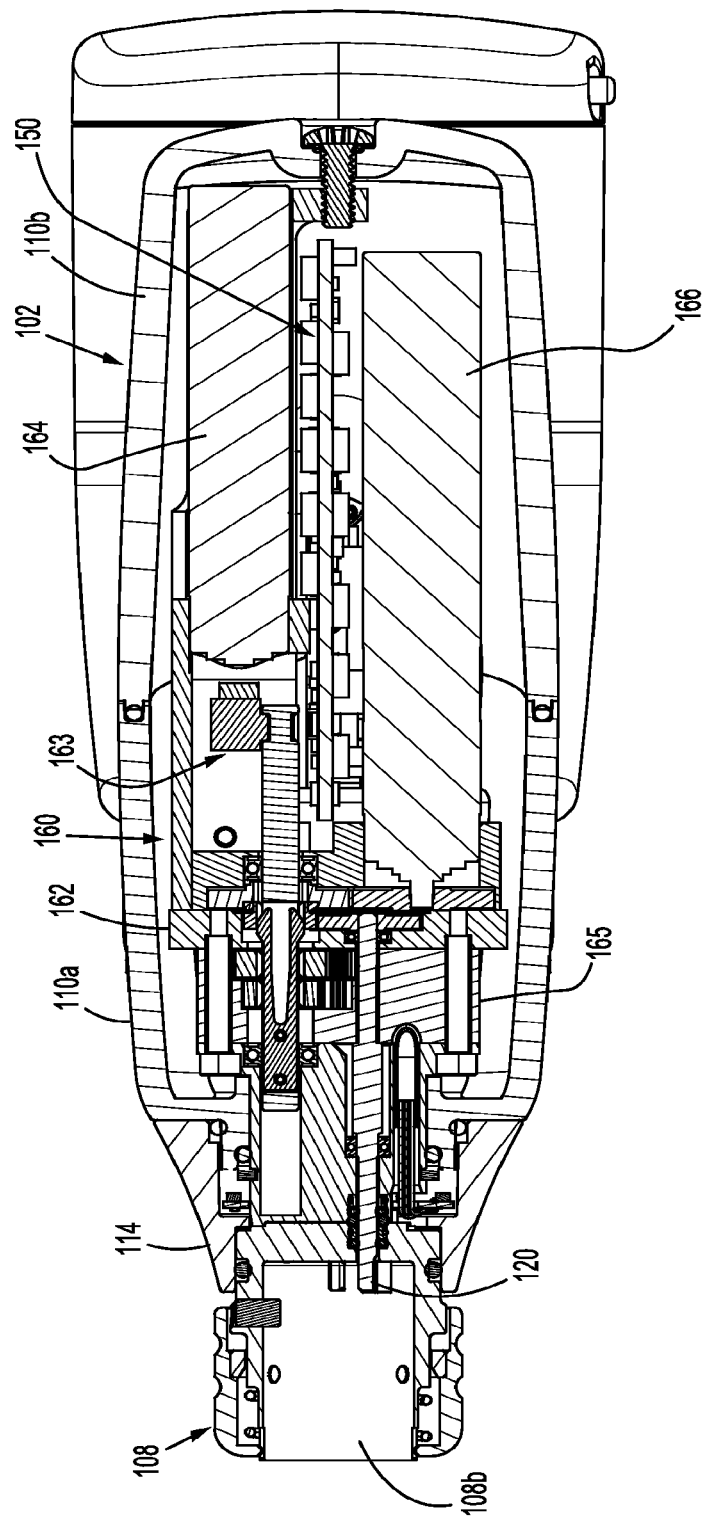
FIG. 8 is a cross-sectional view of the surgical device of FIGS. 1-3, as taken through 8-8 of FIG. 2.

As illustrated in FIGS. 6-8, connecting portion 108a of surgical device 100 has a cylindrical recess 108b that receives a drive coupling assembly 210 of adapter assembly 200 when adapter assembly 200 is mated to surgical device 100. Connecting portion 108a houses three rotatable drive connectors 118, 120, 122.

When a selected adapter assembly 200 is mated to surgical device 100, at least one of the rotatable drive connectors 118, 120, 122 of surgical device 100 couples with a corresponding rotatable connector sleeve, such as, for example connector sleeves 218, 220, 222 of adapter assembly 200 (see FIG. 6). In regard to adapter assembly 200, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter assembly 200.

The mating of drive connectors 118, 120, 122 of surgical device 100 with connector sleeves 218, 220, 222 of adapter assembly 200 allows rotational forces to be independently transmitted via each of the three respective connector interfaces. The drive connectors 118, 120, 122 of surgical device 100 are configured to be independently rotated by drive mechanism 160. In this regard, the function selection module 163 of drive mechanism 160 selects which drive connector or connectors 118, 120, 122 of surgical device 100 is to be driven by the input drive component 165 of drive mechanism 160.

Since each of drive connectors 118, 120, 122 of surgical device 100 has a keyed and/or substantially non-rotatable interface with respective connector sleeves 218, 220, 222 of adapter assembly 200, when adapter assembly 200 is coupled to surgical device 100, rotational force(s) are selectively transferred from drive mechanism 160 of surgical device 100 to adapter assembly 200.

The selective rotation of drive connector(s) 118, 120 and/or 122 of surgical device 100 allows surgical device 100 to selectively actuate different functions of end effector 300. As will be discussed in greater detail below, selective and independent rotation of first drive connector 118 of surgical device 100 corresponds to the selective and independent opening and closing of tool assembly 304 of end effector 300, and driving of a stapling/cutting component of tool assembly 304 of end effector 300. Also, the selective and independent rotation of second drive connector 120 of surgical device 100 corresponds to the selective and independent articulation of tool assembly 304 of end effector 300 transverse to longitudinal axis "X" (see FIG. 3). Additionally, the selective and independent rotation of third drive connector 122 of surgical device 100 corresponds to the selective and independent rotation of end effector 300 about longitudinal axis "X" (see FIG. 3) relative to handle housing 102 of surgical device 100.

As mentioned above and as illustrated in FIGS. 5 and 8, drive mechanism 160 includes a selector gearbox assembly 162; a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical device 100 at a given time.

As illustrated in FIGS. 1-3 and FIG. 9, handle housing 102 supports a trigger housing 107 on a distal surface or side of intermediate housing portion 108. Trigger housing 107, in cooperation with intermediate housing portion 108, supports a pair of finger-actuated control buttons 124, 126 and rocker devices 128, 130. In particular, trigger housing 107 defines an upper aperture 124a for slidably receiving a first control button 124, a lower aperture 126b for slidably receiving a second control button 126, and a includes a fire button or safety switch 132.

Each one of the control buttons 124, 126 and rocker devices 128, 130 and safety switch 132 includes a respective magnet (not shown) that is moved by the actuation of an operator. In addition, circuit board 150 includes, for each one of the control buttons 124, 126 and rocker devices 128, 130, and for the safety switch 132, respective Hall-effect switches 150a-150g that are actuated by the movement of the magnets in the control buttons 124, 126 and rocker devices 128, 130, and safety switch 132.

In particular, located immediately proximal to the control button 124 is a first Hall-effect switch 150c (see FIGS. 3 and 7) that is actuated upon the movement of a magnet within the control button 124 upon the operator actuating control button 124. The actuation of first Hall-effect switch 150c, corresponding to control button 124, causes circuit board 150 to provide appropriate signals to function selection module 163 and input drive component 165 of the drive mechanism 160 to close a tool assembly 304 of end effector 300 and/or to fire a stapling/cutting cartridge within tool assembly 304 of end effector 300.

Also, located immediately proximal to rocker device 128 is a second and a third Hall-effect switch 150b, 150d (see FIGS. 3 and 7) that are actuated upon the movement of a magnet (not shown) within rocker device 128 upon the operator actuating rocker device 128. The actuation of second Hall-effect switch 150b, corresponding to an actuation of rocker device 128 in a first direction, causes circuit board 150 to provide appropriate signals to function selection module 163 and input drive component 165 of drive mechanism 160 to articulate tool assembly 304 relative to body portion 302 of end effector 300 in a relatively left direction. The actuation of third Hall-effect switch 150d, corresponding to an actuation of rocker device 128 in a second direction (opposite the first direction), causes circuit board 150 to provide appropriate signals to function selection module 163 and input drive component 165 of drive mechanism 160 to articulate tool assembly 304 relative to body portion 302 of end effector 300 in a relatively right direction. Advantageously, movement of rocker device 128 in a first direction causes tool assembly 304 to articulate relative to body portion 302 in a first direction, while movement of rocker device 128 in an opposite, e.g., second, direction causes tool assembly 304 to articulate relative to body portion 302 in an opposite, e.g., second, direction.

Furthermore, located immediately proximal to control button 126 is a fourth Hall-effect switch 150ƒ (see FIGS. 3 and 7) that is actuated upon the movement of a magnet (not shown) within control button 126 upon the operator actuating control button 126. The actuation of fourth Hall-effect switch 150ƒ, corresponding to control button 126, causes circuit board 150 to provide appropriate signals to function selection module 163 and input drive component 165 of drive mechanism 160 to open tool assembly 304 of end effector 300.

In addition, located immediately proximal to rocker device 130 is a fifth and a sixth Hall-effect switch 150e, 150g (see FIGS. 3 and 7) that are actuated upon the movement of a magnet (not shown) within rocker device 130 upon the operator actuating rocker device 130. The actuation of fifth Hall-effect switch 150e, corresponding to an actuation of rocker device 130 in a first direction, causes circuit board 150 to provide appropriate signals to function selection module 163 and input drive component 165 of drive mechanism 160 to rotate end effector 300 relative to handle housing 102 of surgical device 100 in a first direction (i.e., counter clockwise). The actuation of sixth Hall-effect switch 150g, corresponding to an actuation of rocker device 130 in a second direction (opposite the first direction), causes circuit board 150 to provide appropriate signals to function selection module 163 and input drive component 165 of drive mechanism 160 to rotate end effector 300 relative to handle housing 102 of surgical device 100 in a second direction (i.e., clockwise). Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

As seen in FIGS. 1-3 and 7, as mentioned above, surgical device 100 includes a fire button or safety switch 132 supported on or in an upper portion of trigger housing 107. In use, tool assembly 304 of end effector 300 is actuated between opened and closed conditions as needed and/or desired. In order to fire end effector 300, to expel fasteners therefrom when tool assembly 304 of end effector 300 is in a closed condition, safety switch 132 is depressed thereby moving a magnet (not shown), supported therein, to actuate a seventh Hall-effect switch 150a, which in turn, instructs surgical device 100 that end effector 300 is ready to expel fasteners therefrom (i.e., places surgical device 100 in a firing mode).

As illustrated in FIGS. 1 and 9-12, surgical device 100 is configured for selective connection with adapter assembly 200, and, in turn, adapter assembly 200 is configured for selective connection with end effector 300. Reference may be made to U.S. patent application Ser. No. 13/484,975, filed on May 31, 2012, entitled "Hand Held Surgical Handle Assembly, Surgical Adapters for Use Between Surgical Handle Assembly and Surgical End Effectors, and Methods of Use," the entire content of which is incorporated herein by reference, for a detailed discussion of the construction and operation of adapter assembly 200.

Adapter assembly 200 is configured to convert a rotation of either of drive connectors 120 and 122 of surgical device 100 into axial translation useful for operating a drive assembly 360 and an articulation link 366 of end effector 300.

Adapter assembly 200 includes a first drive transmitting/converting assembly for interconnecting third rotatable drive connector 122 of surgical device 100 and a first axially translatable drive member of end effector 300, wherein the first drive transmitting/converting assembly converts and transmits a rotation of third rotatable drive connector 122 of surgical device 100 to an axial translation of the first axially translatable drive assembly 360 of end effector 300 for firing.

Adapter assembly 200 includes a second drive transmitting/converting assembly for interconnecting second rotatable drive connector 120 of surgical device 100 and a second axially translatable drive member of end effector 300, wherein the second drive transmitting/converting assembly converts and transmits a rotation of second rotatable drive connector 120 of surgical device 100 to an axial translation of articulation link 366 of end effector 300 for articulation.

Figure 9:
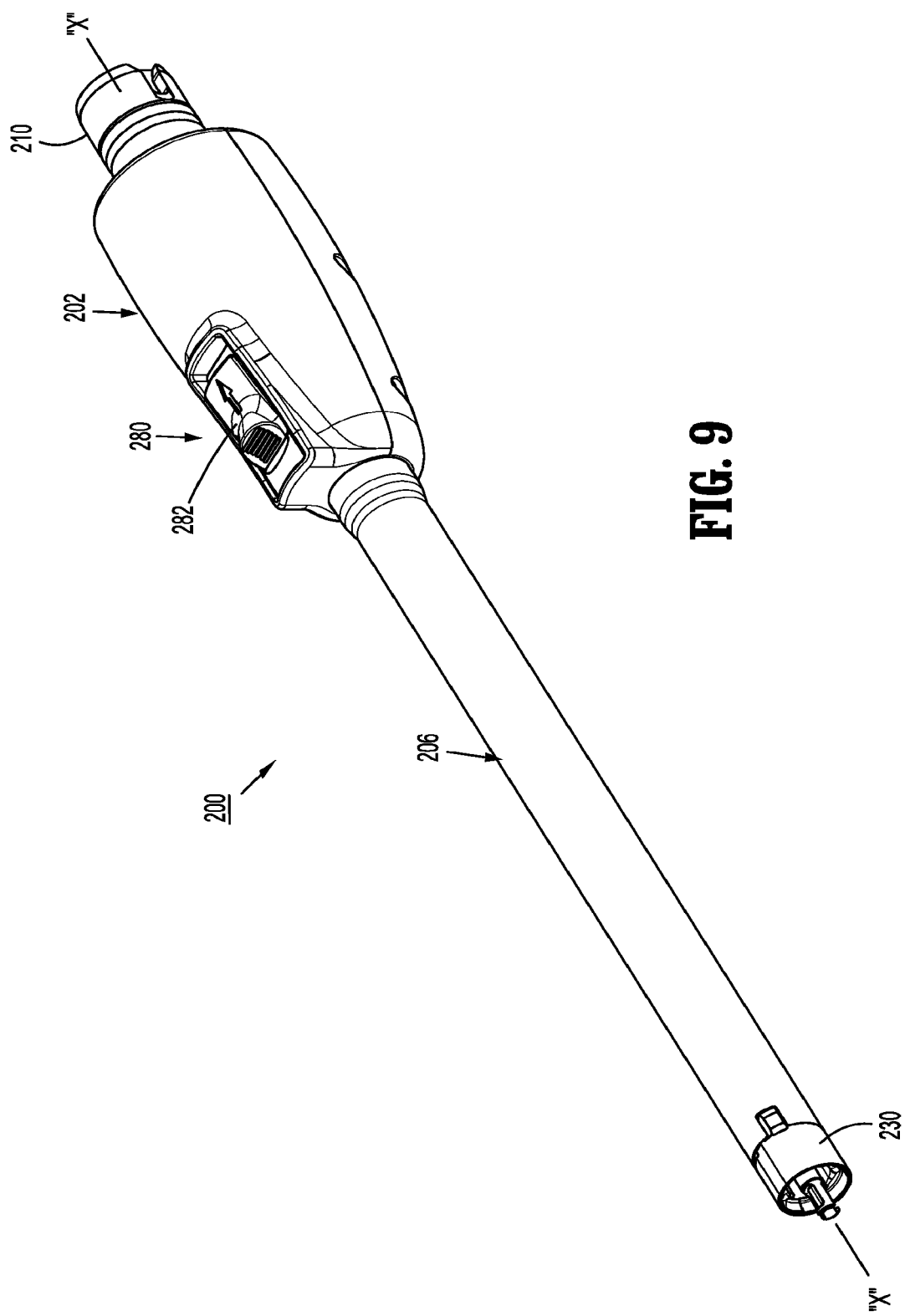
FIG. 9 is a perspective view of the adapter assembly of FIG. 1.
Figure 10:
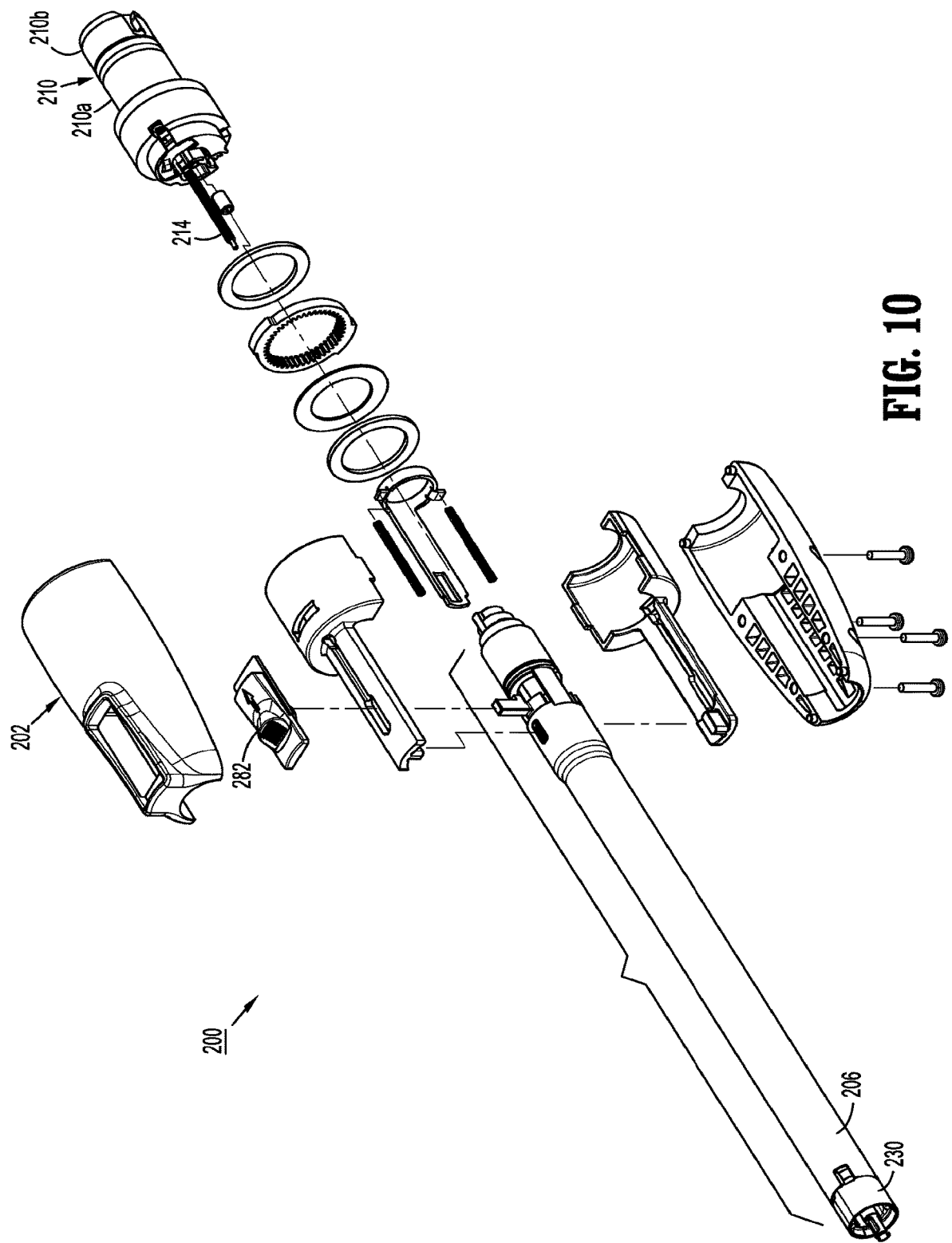
FIG. 10 is a perspective view, with parts separated, of the adapter assembly of FIGS. 1 and 9.

Turning now to FIGS. 9 and 10, adapter assembly 200 includes a knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion, in particular, that outer tube is passable through a typical trocar port, cannula or the like. Knob housing 202 is dimensioned to not enter the trocar port, cannula of the like.

Knob housing 202 is configured and adapted to connect to connecting portion 108a of upper housing portion 108 of distal half-section 110a of surgical device 100.

Figure 11:
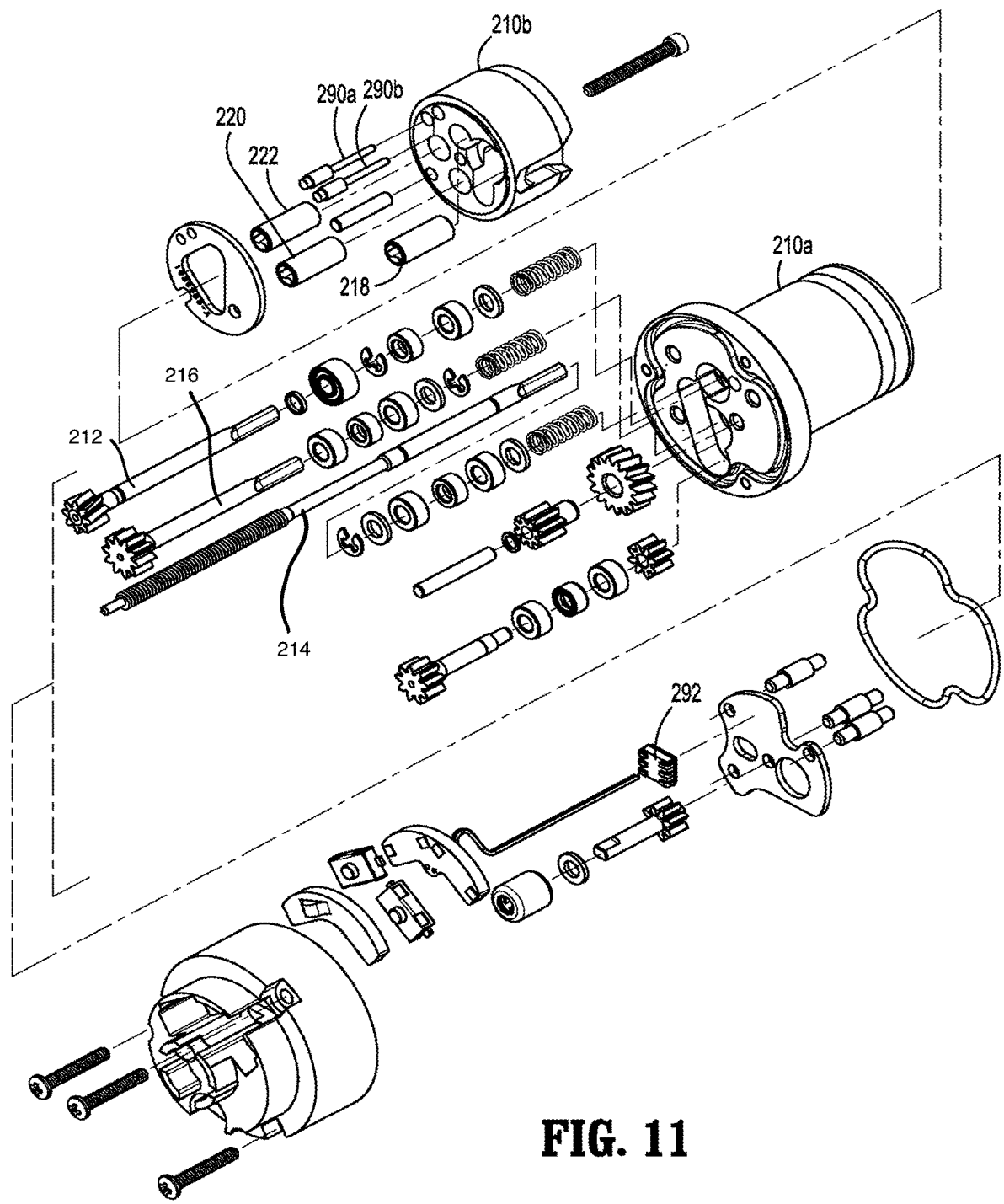
FIG. 11 is a perspective view, with parts separated, of a drive coupling assembly of the adapter assembly of FIGS. 1 and 9.

As seen in FIGS. 9-11, adapter assembly 200 includes a surgical device drive coupling assembly 210 at a proximal end thereof and to an end effector coupling assembly 230 at a distal end thereof. Drive coupling assembly 210 includes a distal drive coupling housing 210a and a proximal drive coupling housing 210b rotatably supported, at least partially, in knob housing 202. Drive coupling assembly 210 rotatably supports a first rotatable proximal drive shaft 212, a second rotatable proximal drive shaft 214, and a third rotatable proximal drive shaft 216 therein.

Proximal drive coupling housing 210b is configured to rotatably support first, second and third connector sleeves 218, 220 and 222, respectively. Each of connector sleeves 218, 220, 222 is configured to mate with respective first, second and third drive connectors 118, 120, 122 of surgical device 100, as described above. Each of connector sleeves 218, 220, 222 is further configured to mate with a proximal end of respective first, second and third proximal drive shafts 212, 214, 216.

Figure 12:
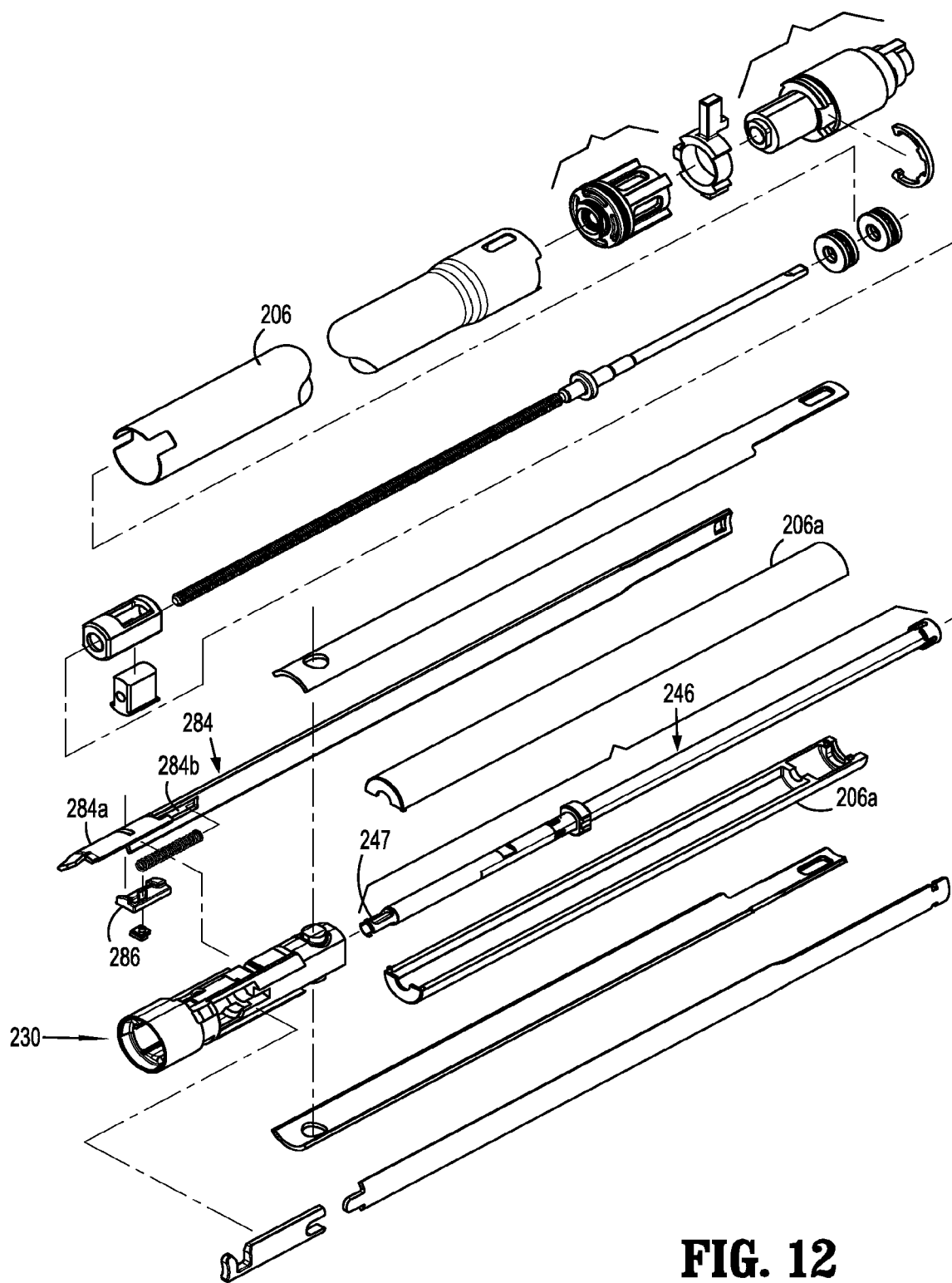
FIG. 12 is a perspective view, with parts separated, of a distal portion of the adapter assembly of FIGS. 1 and 9.

With reference to FIGS. 9 and 12, adapter assembly 200 further includes a lock mechanism for fixing the axial position and radial orientation of drive tube 246 for the connection and disconnection of end effector 300 thereto. The lock mechanism includes a button 282 slidably supported on knob housing 202. Lock button 282 is connected to an actuation bar 284 that extends longitudinally through outer tube 206. Actuation bar 284 is interposed between outer tube 206 and inner housing tube 206a. Actuation bar 284 moves upon a movement of lock button 282. Actuation bar 284 includes a distal portion 284a defining a window 284b therein.

As illustrated in FIG. 12, the lock mechanism further includes a lock out 286 supported on distal coupling assembly 230 at a location in registration with window 284b of distal portion 284a of actuation bar 284. Lock out 286 includes a tab extending toward connection member 247 of drive tube 246. The tab of lock out 286 is configured and dimensioned to selectively engage a cut-out formed in connection member 247 of drive tube 246. Lock mechanism 280 further includes a biasing member 288 tending to maintain lock out 286 and the tab thereof spaced away from the cut-out formed in connection member 247 of drive tube 246.

In operation, in order to lock the position and/or orientation of drive tube 246, a user moves lock button 282 from a distal position to a proximal position, thereby causing a cam surface of actuation bar 284 to engage lock arm 286 and urge lock out 286 toward drive tube 246, against the bias of biasing member 288, such that the tab of lock out 286 is received in the cut-out formed in connection member 247 of drive tube 246. In this manner, drive tube 246 is prevented from distal and/or proximal movement.

When lock button 282 is moved from the proximal position to the distal position, the cam surface is disengaged from lock out 286 thereby allowing biasing member 288 to urge lock out 286 and the tab thereof out of the cut-out formed in connection member 247 of drive tube 246.

As seen in FIGS. 6 and 12, adapter assembly 200 includes a pair of electrical contact pins 290a, 290b for electrical connection to a corresponding electrical plug 190a, 190b disposed in connecting portion 108a of surgical device 100. Electrical contacts 290a, 290b serve to allow for calibration and communication of necessary operating parameters and/or life-cycle information, of adapter assembly 200, to circuit board 150 of surgical device 100 via electrical plugs 190a, 190b that are electrically connected to circuit board 150. Adapter assembly 200 further includes a circuit board 292 supported in knob housing 202 and which is in electrical communication with electrical contact pins 290a, 290b. Circuit board 292 of adapter assembly 200 stores the operating parameters and/or life cycle information for each unique adapter assembly thereon.

Circuit board 292 may include a volatile and/or non-volatile memory for storing either the operating parameters and/or life cycle information, whether the operating parameters and/or life cycle information is original or updated (during or following use).

It is further contemplated that adapter assembly 200 may include a power source or the like, i.e., battery (not shown) which is electrically connected to circuit board 292. It is contemplated that the battery of adapter assembly 200 may provide power to adapter assembly 200 which is different from any power provided from battery 156 of surgical device 100. For example, the batter of adapter assembly 200 may be used to power any mechanical motors in the adapter assembly, power any visual devices or displays supported on or in adapter assembly, or power any audible devices in the adapter assembly.

In accordance with the present disclosure, the operating parameters for adapter assembly 200 include identification information relating to the adapter assembly (e.g., model number, serial number, etc.); dimensions of the adapter assembly; specific designations for which rotational input received from surgical device 100 will perform which specific function in the adapter assembly; what the maximum force is that can be delivered from surgical device 100 to the adapter assembly; and any other required information.

Additionally, in accordance with the present disclosure, the life-cycle information for adapter assembly 200 may include a number of revolutions experienced by connector sleeves 218, 220, 222 of the adapter assembly; a number of cleaning cycles (e.g., hand-washing, dishwashing, irradiating, sterilizing, autoclaving, with or without cleaning fluids, etc.) of the adapter assembly; an assembly date of the adapter assembly; and any repair/maintenance dates of the shaft assembly.

In use, any or all of the operating parameters and/or the life-cycle information may be transmitted from adapter assembly 200 to surgical device 100, via the electrical interface between electrical plugs 190a, 190b of surgical device 100 and electrical contact pins 290a, 290b of the adapter assembly 200, when adapter assembly 200 and surgical device 100 are connected to one another. Alternatively, any or all of the operating parameters and/or the life-cycle information may be transmitted from adapter assembly 200 to surgical device 100 during a calibration sequence of surgical device 100.

While an electrical interface between surgical device 100 and adapter assembly 200, including electrical plugs 190a, 190b and electrical contact pins 290a, 290b, is shown and described, it is contemplated that any other form or telecommunication is within the scope of the present disclosure, for transmitting any or all of the operating parameters and/or the life-cycle information from adapter assembly 200 to surgical device 100, such as, for example, wireless communication, near-field communication, Blue Tooth communication, etc.

In this manner, in accordance with the present disclosure, as new adapter assemblies are developed for a common surgical device (i.e., surgical device 100), any new unique operating parameters and/or the life-cycle information of the new adapter assembly may be specifically associated therewith and transmitted or communicated to the surgical device when the new adapter assembly is connected thereto or during any calibration sequence of the assembled surgical device 100 and new adapter assembly.

In accordance with the present disclosure, it is contemplated that any or all of the operating parameters and/or the life-cycle information may update automatically, may be manually updated by a technician following each surgical use, wherein the adapter assembly may be electrically connected to a computer interface via electrical contact pins 290a, 290b or other communication interface.

In this manner, surgical device 100, being an intelligent surgical instrument, is able to properly handle new (i.e., not yet developed) adapter assemblies, without having to be pre-programmed with required operating parameters for said new adapter assemblies.

In use, when a button of surgical device 100 is activated by the user, the software checks predefined conditions. If conditions are met, the software controls the motors and delivers mechanical drive to the attached end effector (e.g., surgical stapler), via an adapter assembly, which can then open, close, rotate, articulate or fire depending on the function of the pressed button. The software also provides feedback to the user by turning colored lights on or off in a defined manner to indicate the status of surgical device 100, adapter assembly 200 and/or end effector 300.

A high level electrical architectural view of the system is displayed below in Schematic "A" and shows the connections to the various hardware and software interfaces. Inputs from presses of buttons 124, 126 and from motor encoders of the drive shaft are shown on the left side of Schematic "A". The microcontroller contains the device software that operates surgical device 100, adapter assembly 200 and/or end effector 300. The microcontroller receives inputs from and sends outputs to a MicroLAN, an Ultra ID chip, a Battery ID chip, and Adaptor ID chips.

The MicroLAN, the Ultra ID chip, the Battery ID chip, and the Adaptor ID chips control surgical device 100, adapter assembly 200 and/or end effector 300 as follows:

| | |
|---|---|
| MicroLAN - | Serial 1-wire bus communication to read/write system component ID information. |
| Ultra ID chip - | identifies surgical device 100 and records usage information. |
| Battery ID chip - | identifies the Battery 156 and records usage information. |
| Adaptor ID chip assembly 200, - | identifies the type of adapter records the presence of an end effector 300, and records usage information. |

Figure 13:
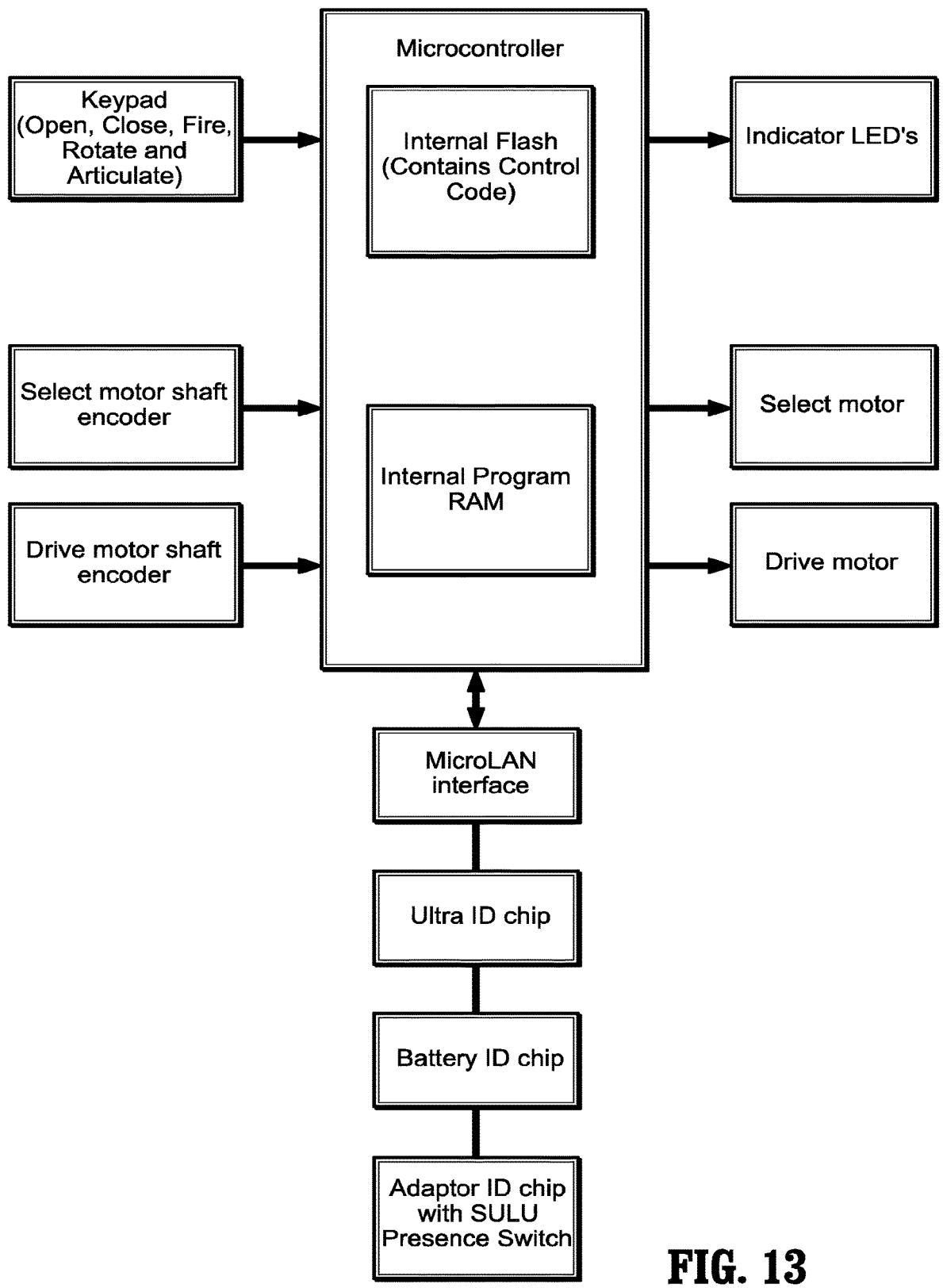
FIG. 13 is a schematic illustration of the outputs to the LED's; selection of motor (to select clamping/cutting, rotation or articulation); and selection of the drive motors to perform a function selected.

The right side of the schematic illustrated in FIG. 13 indicates outputs to the LED's; selection of motor (to select clamping/cutting, rotation or articulation); and selection of the drive motors to perform the function selected.

As illustrated in FIG. 1, the end effector is designated as 300. End effector 300 is configured and dimensioned for endoscopic insertion through a cannula, trocar or the like. In particular, in the embodiment illustrated in FIG. 1, end effector 300 may pass through a cannula or trocar when end effector 300 is in a closed condition.

End effector 300 includes a proximal body portion 302 and a tool assembly 304. Proximal body portion 302 is releasably attached to a distal coupling 230 of adapter assembly 200 and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar.

Reference may be made to U.S. Pat. No. 7,819,896, filed on Aug. 31, 2009, entitled "TOOL ASSEMBLY FOR A SURGICAL STAPLING DEVICE", the entire content of which is incorporated herein by reference, for a detailed discussion of the construction and operation of end effector 300.

Since adapter assembly 200 is reusable, prior to each use, at least adapter assembly 200 must be sterilized using known sterilization techniques and methods (e.g., hand-washing, dishwashing and/or then autoclaving using cleaning fluids or the like).

Figure 14:
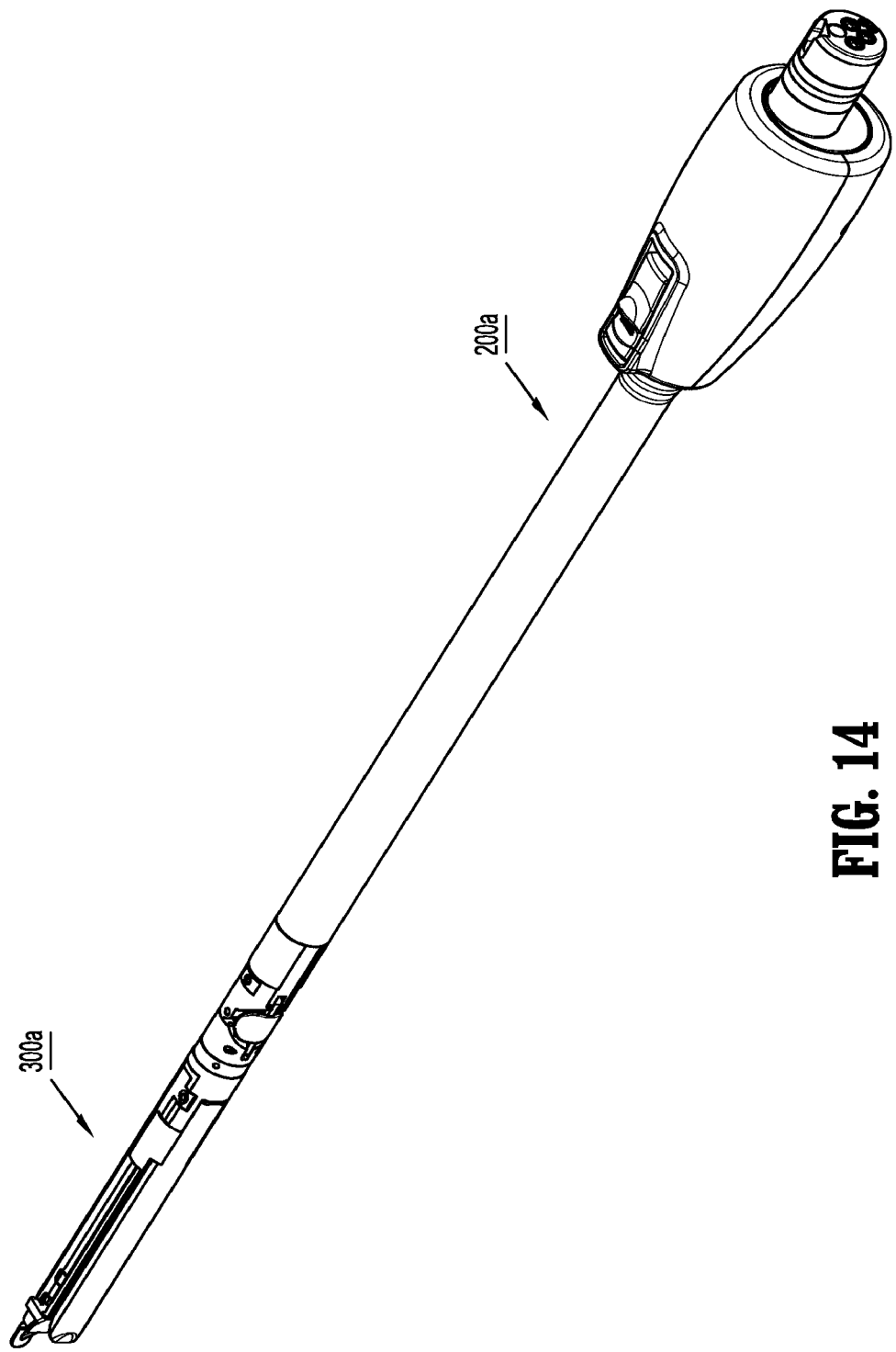
FIG. 14 is a rear, perspective view of an alternate embodiment of an adapter assembly and an alternate embodiment of an end effector incorporating novel aspects of the present disclosure, for use with the hand-held, electromechanical surgical device of FIG. 1.
Figure 15:
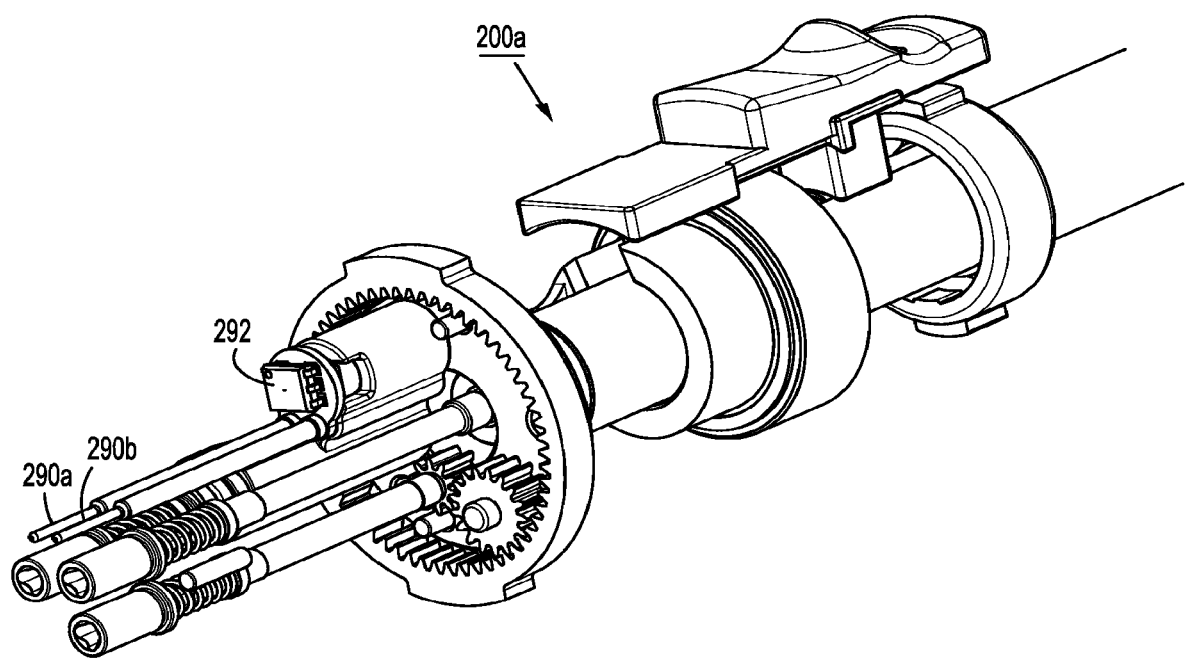
FIG. 15 is a rear, perspective view of a proximal portion of the adapter assembly of FIG. 14, with a housing removed therefrom.

Turning now to FIGS. 14-15, an alternate embodiment of an adapter assembly 200a and an alternate embodiment of an end effector 300a, incorporating novel aspects of the present disclosure, for use with the hand-held, electromechanical surgical device 100, is shown. Reference may be made to U.S. patent application Ser. No. 13/769,419, filed on Feb. 18, 2013, entitled "APPARATUS FOR ENDOSCOPIC PROCEDURES", the entire content of which is incorporated herein by reference in its entirety, for a detailed discussion of the construction and operation of adapter assembly 200a and end effector 300a.

As seen specifically in FIG. 15, adapter assembly 200a includes a circuit board 292 and electrical contacts 290a, 290b, similar to adapter assembly 200.

While the specific operation and functionality of adapter assembly 200a may be different than adapter assembly 200, in order to operate end effector 300a, circuit board 292 of adapter assembly 200a may store operating parameters and/or life cycle information which is/are unique to adapter assembly 200a.

Reference may additionally be made to U.S. patent application Ser. No. 13/769,414, filed on Feb. 18, 2013, entitled "APPARATUS FOR ENDOSCOPIC PROCEDURES"; and to U.S. patent application Ser. No. 13/799,379, filed on Mar. 13, 2013, entitled "APPARATUS FOR ENDOSCOPIC PROCEDURES", the entire content of each of which being incorporated herein by reference in their entirety, for a detailed discussion of the construction and operation of alternate adapter assemblies and/or end effectors, incorporating novel aspects of the present disclosure, for use with the hand-held, electromechanical surgical device 100.

In accordance with the present disclosure, it is contemplated that an operating room or the like would be supplied with an electromechanical surgical system including at least one surgical device 100; a plurality of unique and/or diverse adapter assemblies, in accordance with the present disclosure; and a plurality of diverse end effectors, capable of performing a number of different surgical procedures. In use, depending on the surgical procedure to be performed, the surgeon will select a desired and appropriate end effector for performing the particular surgical procedure; the surgeon will select an appropriate adapter assembly for interconnecting the particular end effector and the surgical device 100; and the surgeon (or other operating room staff) will connect the appropriate adapter assembly to the surgical device 100.

It is then contemplated that the appropriate adapter assembly will communicate with surgical device 100, wherein the operating parameters and/or life cycle information for the appropriate adapter assembly will be transmitted or communicated from circuit board 292 of the appropriate adapter assembly to surgical device 100 for processing thereby. If the operating parameters and/or life cycle information for the appropriate adapter assembly produce no error signals from surgical device 100, during a calibration and/or initialization sequence, surgical device 100 may produce a ready signal, whereby the surgeon (or other operating room staff) will connect the selected end effector to the appropriate adapter assembly.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An electromechanical surgical system comprising:
   an end effector configured to perform a plurality of functions;
   a surgical device including a plurality of drive connectors; and
   an adapter assembly configured to couple to the surgical device and the end effector, the adapter assembly including:
   a plurality of drive shafts interconnecting the plurality of drive connectors and the end effector, such that actuation of one drive connector of the plurality of drive connectors actuates the end effector to perform a corresponding function of the plurality of functions; and
   a memory storing a specific designated function of the plurality of functions for each drive shaft of the plurality of drive shafts.

2. The electromechanical surgical system according to claim 1, wherein the memory further stores at least one operating parameter pertaining to the adapter assembly.

3. The electromechanical surgical system according to claim 2, wherein the at least one operating parameter is at least one of dimensions of the adapter assembly, or a maximum force that can be delivered from the surgical device to the adapter assembly.

4. The electromechanical surgical system according to claim 1, wherein the memory further stores identification information relating to the adapter assembly.

5. The electromechanical surgical system according to claim 4, wherein the identification information includes at least a model number and a serial number.

6. The electromechanical surgical system according to claim 1, wherein the memory further stores life-cycle information pertaining to the adapter assembly.

7. The electromechanical surgical system according to claim 6, wherein the life cycle information includes at least one of:
- a number of revolutions experienced by each drive shaft of the plurality of drive shafts;
- a number of cleaning cycles of the adapter assembly;
- an assembly date of the adapter assembly; or
- a repair or maintenance date of the adapter assembly.

8. The electromechanical surgical system according to claim 1, wherein the adapter assembly further includes at least one electrical contact configured to interface with the surgical device.

9. The electromechanical surgical system according to claim 1, wherein the adapter assembly is releasably connectable to the surgical device and the end effector.

10. An electromechanical surgical system comprising:
- an end effector configured to perform a plurality of functions including rotation of the end effector about a longitudinal axis, articulation of the end effector about an axis transverse to the longitudinal axis, and closing of the end effector;
- a surgical device including a plurality of drive connectors; and
- an adapter assembly configured to couple to the surgical device and the end effector, the adapter assembly including:
  - a plurality of drive shafts interconnecting the plurality of drive connectors and the end effector, each of the drive shafts configured to convert rotational motion into linear motion, such that actuation of one drive connector of the plurality of drive connectors actuates the end effector to perform a corresponding function of the plurality of functions; and
  - a memory storing a specific designated function of the plurality of functions for each drive shaft of the plurality of drive shafts.

11. The electromechanical surgical system according to claim 10, wherein the memory further stores at least one operating parameter pertaining to the adapter assembly.

12. The electromechanical surgical system according to claim 11, wherein the at least one operating parameter is at least one of dimensions of the adapter assembly, or a maximum force that can be delivered from the surgical device to the adapter assembly.

13. The electromechanical surgical system according to claim 12, wherein the memory further stores identification information relating to the adapter assembly.

14. The electromechanical surgical system according to claim 13, wherein the identification information includes at least a model number and a serial number.

15. The electromechanical surgical system according to claim 10, wherein the memory further stores life-cycle information pertaining to the adapter assembly.

16. The electromechanical surgical system according to claim 15, wherein the life cycle information includes at least one of:
- a number of revolutions experienced by each drive shaft of the plurality of drive shafts;
- a number of cleaning cycles of the adapter assembly;
- an assembly date of the adapter assembly; or
- a repair or maintenance date of the adapter assembly.

17. The electromechanical surgical system according to claim 10, wherein the adapter assembly further includes at least one electrical contact configured to interface with the surgical device.

* * * * *